(12) United States Patent
Rahman et al.

(10) Patent No.: US 12,147,428 B2
(45) Date of Patent: Nov. 19, 2024

(54) SYSTEM AND METHOD FOR SEARCHING TIME SERIES DATA (71) Applicant: KONINKLIJKE PHILIPS N.V., Eindhoven (NL)

(72) Inventors: Asif Rahman, Eindhoven (NL); Bryan Conroy, Eindhoven (NL); Yale Chang, Sevenum (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 18/282,813

(22) PCT Filed: Apr. 2, 2022

(86) PCT No.: PCT/EP2022/058821
§ 371 (c)(1),
(2) Date: Sep. 19, 2023

(87) PCT Pub. No.: WO2022/214409
PCT Pub. Date: Oct. 13, 2022

(65) Prior Publication Data
US 2024/0168952 A1    May 23, 2024

Related U.S. Application Data
(60) Provisional application No. 63/170,753, filed on Apr. 5, 2021.

(51) Int. Cl.
G06F 16/2455 (2019.01)
G06F 16/22 (2019.01)
G06F 16/2453 (2019.01)
G06F 16/248 (2019.01)
G16H 10/60 (2018.01)

(52) U.S. Cl.
CPC .......... *G06F 16/2455* (2019.01); *G06F 16/22* (2019.01); *G06F 16/24542* (2019.01); *G06F 16/248* (2019.01); *G16H 10/60* (2018.01)

(58) Field of Classification Search
None
See application file for complete search history.

(56) References Cited

U.S. PATENT DOCUMENTS

| | | | |
|---|---|---|---|
| 11,610,126 B1* | 3/2023 | Heckerman | G06N 20/10 |
| 2023/0018125 A1* | 1/2023 | Lim | G06N 3/08 |
| 2023/0039740 A1* | 2/2023 | Wang | G06N 3/0442 |
| 2023/0229963 A1* | 7/2023 | Iyer | G06N 20/00 |
| | | | 706/12 |

* cited by examiner

Primary Examiner — Irene Baker (57) ABSTRACT

A method (100) for identifying time series data using a time series retrieval system (800), comprising: receiving (120) a plurality of time series, each time series comprising a plurality of datapoints, wherein a least some of the plurality of times series comprise datapoints obtained at irregular time intervals within the time period; storing (130) the received plurality of time series in a database; generate (140) a context vector for each of the plurality of time series; receiving (150) a request for identification of one or more of the plurality of time series based on similarity to a time series query; identifying (160), based on similarity to the query time series context vector, one or more of the stored generated context vectors; retrieving (170) each time series associated with the identified one or more stored generated context vectors; and providing (180) the retrieved time series.

15 Claims, 9 Drawing Sheets

SYSTEM AND METHOD FOR SEARCHING TIME SERIES DATA

CROSS-REFERENCE TO PRIOR APPLICATIONS

This application is the U.S. National Phase application under 35 U.S.C. § 371 of International Application No. PCT/EP2022/058821, filed on Apr. 2, 2022, which claims the benefit of U.S. Provisional Application No. 63/170,753 filed on Apr. 5, 2021. These applications are hereby incorporated by reference herein.

FIELD OF THE INVENTION

The present disclosure is directed generally to systems and methods for identifying and retrieving stored time series data.

BACKGROUND

Time series data comprise repeated observations made sequentially from sensors, business processes, information systems, and other data-gathering processes. These time series are routinely collected in the real world. However, often a time series contains gaps in the data collection for a variety of reasons, including hardware failure, planned or unplanned disruptions to signal acquisition systems, or simply due to the cadence of the practice of acquiring the information. Indeed, most real-world data are irregularly sampled, contain missing data, and are of variable length.

As just one example of time series data, clinical time series data are known to be very informative for patient conditions. For example, clinicians track temporal trends of vitals to monitor patients over time. However, these vitals are most often obtained at irregular time periods, resulting in imperfect time series data. In addition to the clinical setting, there are many, many other examples of irregular time series data.

Given imperfect time series data, it can be challenging to identify a time series based on, for example, similarity to a query. Being able to search a database of stored time series data to identify similar patterns to a query time series can be advantageous. Indeed, there are many use cases where identifying similar or identical time series data is desirable.

One such use case is to utilize historical patient data to identify patients that may share a similar disease progression to a query patient, thereby allowing comparison of demographics, clinical outcomes, and other important clinical metrics. For example, a user may want to identify patients in order to conduct a user study by showing example patients to physicians and conducting a survey. The user has in mind certain types of patients, for example patients that had a stable risk score and then started to deteriorate starting three hours before an intervention was given. Or a patient that was stable over a six-hour period but suddenly their status deteriorated leading to death. Such specific queries are commonplace and very difficult to achieve without manual annotation and writing rules to retrieve patients that match specific hard-coded criteria. Although this use case is a clinical healthcare use case, it is appreciated that many other use cases in many other fields are known in the art.

SUMMARY OF THE INVENTION

Accordingly, there is a continued need in the art for systems and methods that enable the rapid and accurate retrieval of stored irregular time series data based on similarity to a query time series.

The present disclosure is directed to inventive methods and systems for the identification of stored time series data using a time series retrieval system. The system receives a plurality of time series, each time series comprising a plurality of datapoints obtained over a time period. At least some of the plurality of times series comprise datapoints obtained at irregular time intervals within the time period. The received time series data is stored in a database of the time series retrieval system. Each of the received plurality of time series is then converted to a context vector using a trained time series encoder/decoder of the time series retrieval system, and the generated context vector is stored in a database of the time series retrieval system. To retrieve stored time series data, the system first receives a request for identification of one or more of the plurality of time series based on similarity to a time series query. The system identifies one or more of the stored generated context vectors based on similarity to the query time series context vector. The trained time series encoder/decoder of the time series retrieval system retrieves each stored time series associated with the identified one or more stored generated context vectors, and then provides the retrieved time series data to a user via a user interface of the time series retrieval system.

Generally, in example one, a method for identifying time series data using a time series retrieval system is provided. The method includes: (i) receiving, by the time series retrieval system, a plurality of time series, each time series comprising a plurality of datapoints obtained over a time period, wherein a least some of the plurality of times series comprise datapoints obtained at irregular time intervals within the time period; (ii) storing the received plurality of time series in a time series database of the time series retrieval system; (iii) for each of the received plurality of time series: normalize each of the plurality of datapoints of the time series; concatenate, with each of the normalized plurality of datapoints, a time interval between the respective datapoint and an immediately preceding datapoint; generate from the normalized and concatenated time series, using a trained time series encoder/decoder of the time series retrieval system, a context vector for the time series; and store the generated context vector in a database of the time series retrieval system; (iv) receiving a request for identification of one or more of the plurality of time series based on similarity to a time series query, comprising: receiving, via a user interface of the time series retrieval system, a query time series; and generating, using the trained time series encoder of the time series retrieval system, a query time series context vector; (v) identifying, based on similarity to the query time series context vector, one or more of the stored generated context vectors; (vi) retrieving, from the time series database, each of the time series represented by the identified one or more stored generated context vectors; and (vii) providing, via the user interface of the time series retrieval system, the retrieved time series.

In embodiments, example one may be combined with example two, wherein the time series encoder/decoder of the time series retrieval system is trained. Training the time series encoder/decoder includes reiteration of: (i) receiving a training time series dataset comprising a plurality of time series, each time series in the training time series dataset comprising a plurality of datapoints obtained over a time period, wherein at least some of the plurality of times series in the training time series dataset comprise datapoints obtained at irregular time intervals within the time period; (ii) encoding, using the encoder/decoder of the time series retrieval system, a training time series of the training time series dataset to a context vector; (iii) decoding, using the encoder/decoder of the time series retrieval system, the context vector to generate a decoded time series; (iv) comparing the decoded time series to the original unencoded time series; (v) adjusting the encoder/decoder of the time series retrieval system, if the decoded time series does not sufficiently match the original unencoded time series; and (vi) storing the adjusted encoder/decoder of the time series retrieval system.

In embodiments, examples one or two may be combined with example three, wherein the trained time series encoder comprises a neural network.

In embodiments, example three may be combined with example four, wherein the neural network is a bidirectional long short-term memory recurrent neural network.

In embodiments, examples one, two, three, or four may be combined with example five, wherein the one or more stored generated context vectors are identified based on a nearest neighbor method.

In embodiments, examples one, two, three, four, or five may be combined with example six, wherein each stored generated context vector is associated in memory with contextual information about the time series used to create the context vector.

In embodiments, examples one, two, three, four, five, or six may be combined with example seven, wherein each of the plurality of time series comprises a plurality of datapoints obtained over a time period from a respective patient in a clinical setting.

In embodiments, examples one, two, three, four, five, six, or seven may be combined with example eight, wherein the query time series is generated by a user drawing a time series via the user interface of the time series retrieval system.

Generally, in example nine, a time series retrieval system is provided. The system includes a plurality of time series stored in a time series database, each time series comprising a plurality of datapoints obtained over a time period, wherein a least some of the plurality of times series comprise datapoints obtained at irregular time intervals within the time period; a trained encoder/decoder configured to generate a context vector for each of the plurality of time series, resulting in a plurality of generated context vectors; a database configured to store the plurality of plurality of generated context vectors; a processor configured to: (i) receive a request for identification of one or more of the plurality of time series based on similarity to a time series query; (ii) identify, based on similarity to the query time series context vector, one or more of the plurality of generated context vectors, and wherein the trained encoder/decoder is further configured to retrieve from the time series database each of the time series represented by the identified one or more generated context vectors, and a user interface, wherein the user interface is configured to receive the time series query, and further configured to provide the retrieved time series.

In embodiments, example nine may be combined with example ten, wherein the trained time series encoder comprises a neural network.

In embodiments, example ten may be combined with example eleven, wherein the neural network is a bidirectional long short-term memory recurrent neural network.

In embodiments, examples, nine, ten, or eleven may be combined with example twelve, wherein the one or more stored generated context vectors are identified based on a nearest neighbor method.

In embodiments, examples nine, ten, eleven, or twelve may be combined with example thirteen, wherein each stored generated context vector is associated in memory with contextual information about the time series used to create the context vector.

In embodiments, examples nine, ten, eleven, twelve, or thirteen may be combined with example fourteen, wherein each of the plurality of time series comprises a plurality of datapoints obtained over a time period from a respective patient in a clinical setting.

In embodiments, examples nine, ten, eleven, twelve, thirteen, or fourteen may be combined with example fifteen, wherein the query time series is generated by a user drawing a time series via the user interface of the time series retrieval system.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the various embodiments will be apparent from and elucidated with reference to the embodiment(s) described hereinafter.

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

In one network implementation, one or more devices coupled to a network may serve as a controller for one or more other devices coupled to the network (e.g., in a master/slave relationship). In another implementation, a networked environment may include one or more dedicated controllers that are configured to control one or more of the devices coupled to the network. Generally, multiple devices coupled to the network each may have access to data that is present on the communications medium or media; however, a given device may be "addressable" in that it is configured to selectively exchange data with (i.e., receive data from and/or transmit data to) the network, based, for example, on one or more particular identifiers (e.g., "addresses") assigned to it.

The term "network" as used herein refers to any interconnection of two or more devices (including controllers or processors) that facilitates the transport of information (e.g. for device control, data storage, data exchange, etc.) between any two or more devices and/or among multiple devices coupled to the network. As should be readily appreciated, various implementations of networks suitable for interconnecting multiple devices may include any of a variety of network topologies and employ any of a variety of communication protocols. Additionally, in various networks according to the present disclosure, any one connection between two devices may represent a dedicated connection between the two systems, or alternatively a non-dedicated connection. In addition to carrying information intended for the two devices, such a non-dedicated connection may carry information not necessarily intended for either of the two devices (e.g., an open network connection). Furthermore, it should be readily appreciated that various networks of devices as discussed herein may employ one or more wireless, wire/cable, and/or fiber optic links to facilitate information transport throughout the network.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of a time series retrieval system configured to identify stored time series data. More generally, Applicant has recognized that it would be beneficial to provide a method and system that facilitates rapid and easy searching of time series data. In view of the foregoing, various embodiments and implementations are directed to a time series retrieval system configured to enable retrieval of relevant stored time series data based on similarity to a time series query. The system receives a plurality of time series, each time series comprising a plurality of datapoints obtained over a time period. At least some of the plurality of times series comprise datapoints obtained at irregular time intervals within the time period. The received time series data is stored in a time series database of the time series retrieval system. Each of the received plurality of time series is then converted to a context vector using a trained time series encoder/decoder of the time series retrieval system, and the generated context vector is stored in a database of the time series retrieval system. To retrieve stored time series data, the system first receives a request for identification of one or more of the plurality of time series based on similarity to a time series query. The system identifies one or more of the stored generated context vectors based on similarity to the query time series context vector. The trained time series encoder/decoder of the time series retrieval system retrieves from the time series database each stored time series associated with the identified one or more identified generated context vectors, and then provides the retrieved time series data to a user via a user interface of the time series retrieval system.

The time series encoder/decoder of the time series retrieval system must be trained. According to an embodiment, the time series retrieval system receives a training time series dataset comprising a plurality of time series, each time series in the training time series dataset comprising a plurality of datapoints obtained over a time period. As expected, at least some of the plurality of times series in the training time series dataset comprise datapoints obtained at irregular time intervals within the time period. The encoder/decoder of the time series retrieval system encodes each of the time series in the training time series dataset, thereby generating a context vector for each time series. This context vector can be stored or utilized immediately. The encoder/decoder of the time series retrieval system then decodes the context vector to generate a decoded time series, and the system compares the decoded time series to the original unencoded time series in order to evaluate the accuracy of the encoder/decoder. If the decoded time series does not match or does not sufficiently match the original unencoded time series, the encoder/decoder can be adjusted. The modified encoder/decoder is then stored and utilized for the next iteration of the training process.

Accordingly, the time series retrieval system comprises a method for training of a time series encoder/decoder, and the identification and retrieval of stored time series data based on similarity to a query time series. Thus, the system utilizes a database of irregularly sampled time series, such as vital signs or laboratory measurements, and passes each time series through a sequence-to-sequence autoencoder specifically designed to encode irregular time series. The encoded signal vector is then stored in a database for later retrieval.

Figure 1:
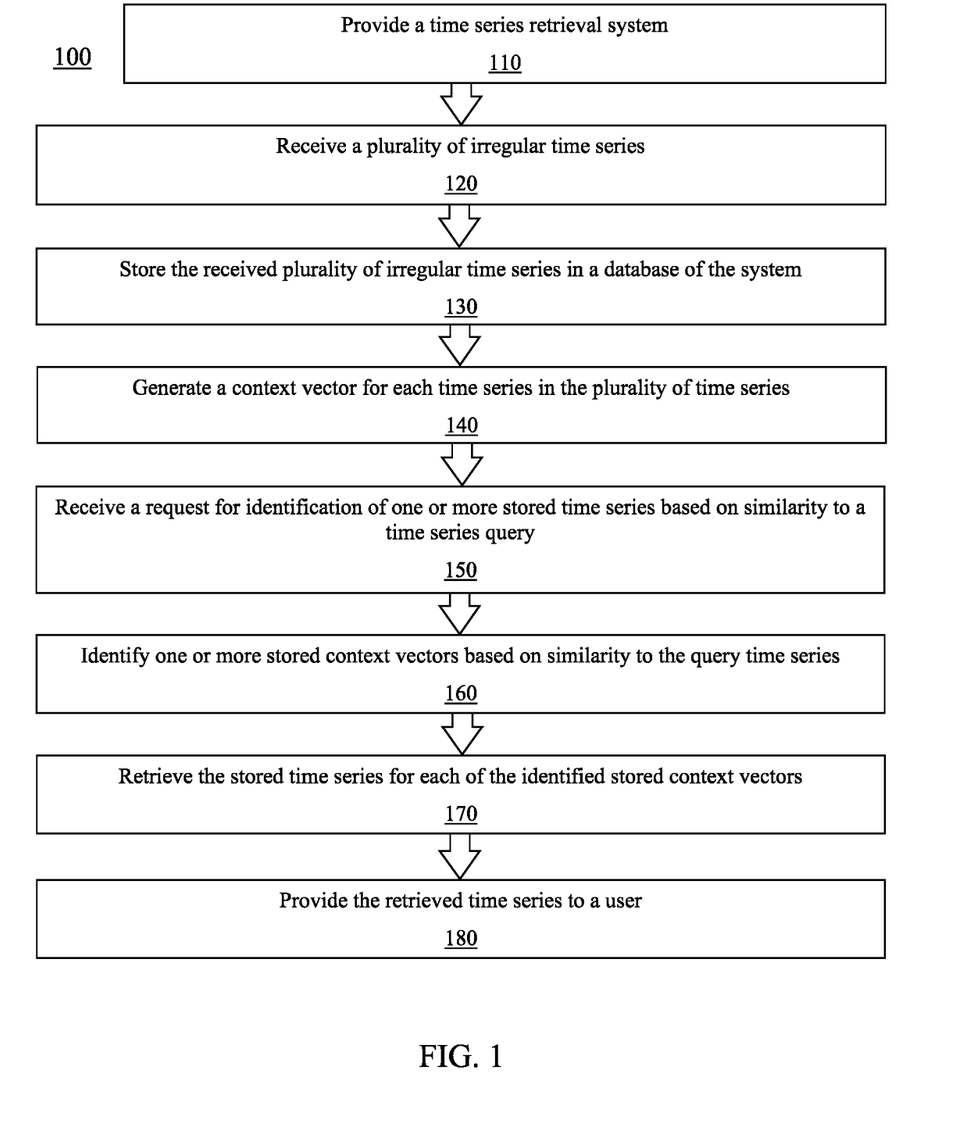
FIG. 1 is a flowchart of a method for identifying time series data using a time series retrieval system, in accordance with an embodiment.

Referring to FIG. 1 is a flowchart of a method 100 for identifying time series data using a time series retrieval system. At step 110 of the method, a time series retrieval system is provided. The time series retrieval system can be any of the systems described or otherwise envisioned herein. According to one embodiment, the time series retrieval system can be a local system, a remote system such as a cloud-based system, or a combination of local and cloud-based.

At step 120 of the method, the time series retrieval system receives a plurality of time series. A time series can be any series of two or more datapoints obtained over a period of time. The datapoints can be any data, and the period of time can be of any length sufficient for the collection of two or more datapoints. The datapoints can be collected using any method of collecting data, such as sensor data, manual entry of information, or any other data collection or identification method. As just one example, the datapoints in a time series may be vital signs, lab measurements, or other clinical data obtained from or about a patient. Vital signs such as heart rate, blood pressure, $SpO_2$, and/or laboratory values such as hemoglobin, hematocrit, lactate, calcium, and other measurements are just a few of an unlimited number of examples. According to another example, the datapoints may be weather records, financial data, business records, or any of a vast multitude of different sources of data.

According to a preferred embodiment, the database comprises time series data obtained from a similar sensor, data collection method, or other related process or methodology. However, according to another embodiment the database may comprise time series data that may be unrelated, or may appear to be unrelated.

According to an embodiment, some or all of the plurality of time series comprise datapoints obtained at irregular time intervals within the time period. For example, a time series of blood pressure measurements obtained from a patient may comprise three datapoints taken over the course of one hour, or three blood pressure measurements with the first measurement initiating the time period and the third time period terminating the time period. Perfect time series data would comprise a second blood pressure measurement that is located at the exact midpoint of the first and third measurement, or at 30 minutes after the first measurement and 30 minutes before the third measurement. However, so-called perfect time series data is extremely rare in practice. Accordingly, as one example the second measurement may be obtained from a first patient 20 minutes after the first measurement and thus 40 minutes before the third measurement. Similarly, a second measurement may be obtained from a second patient 45 minutes after the first measurement and thus 15 minutes before the third measurement. These two time series are thus irregular compared to each other. Indeed, comparing the time series of the first patient to the time series of the second patient is imperfect and challenging using prior art time series analysis methods and systems.

At step 130 of the method, the received plurality of time series are stored in a time series database. The time series database may be a local and/or remote database. For example, the time series retrieval system may comprise a database of stored time series data.

Figure 2:
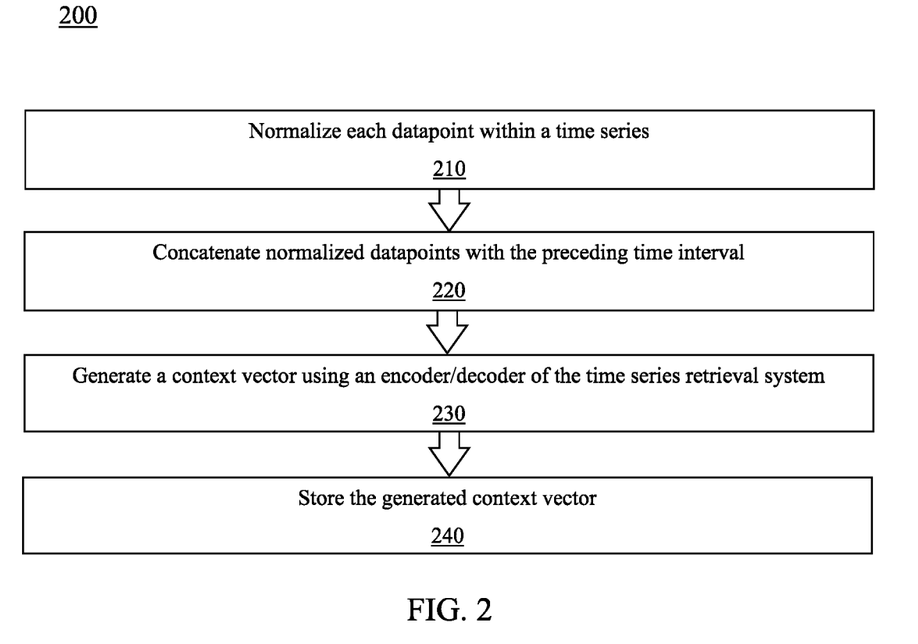
FIG. 2 is a flowchart of a method for generating a context vector by a time series retrieval system, in accordance with an embodiment.

At step 140 of the method, the time series retrieval system generates, using a trained time series encoder/decoder of the time series retrieval system, a context vector for each time series in the plurality time series. Referring to FIG. 2 is a method 200 for generating and storing a context vector for a time series using a trained time series encoder/decoder of the time series retrieval system. At step 210 of the method, the system normalizes each of the plurality of datapoints of a time series to a value between 0 and 1. This can be performed utilizing any method or algorithm for normalizing data. At step 220 of the method, some or all of the normalized datapoints are concatenated with the time interval, or lag, between a respective datapoint and an immediately preceding datapoint. At step 230 of the method, a trained time series encoder/decoder of the time series retrieval system is utilized to generate a context vector from the normalized and concatenated time series. The context vector may be of any length. According to an embodiment, the context vector comprises a length of 8, but any other length is possible and may depend in part or in whole on the data, the trained encoder/decoder, user parameters, and/or any other parameter. The encoder/decoder may be any machine learning algorithm, neural network, or other methodology configured to convert a normalized and concatenated time series into a context vector or other numeric representation. Training of the time series encoder/decoder is described in detail elsewhere herein. At step 240 of method 200, the generated context vector is stored in a database of the time series retrieval system. The database may be a local and/or remote database. For example, the time series retrieval system may comprise a database of context vectors.

Returning to FIG. 1, at step 150 of method 100 the time series retrieval system receives a request for identification of one or more of the plurality of context vector-based stored time series based on similarity to a time series query. According to an embodiment, a user interface of the time series retrieval system receives a query time series. The trained encoder/decoder of time series retrieval system then generates a query time series context vector from the received query time series, and this generated query time series context vector can be utilized in a subsequent step of the method to query the database.

According to an embodiment, the query time series can be provided to the time series retrieval system utilizing any method for providing time series data. As an example, a user may provide a series of datapoints representing a time series, such as a series of two or more measurements along with time intervals between each of the two or more measurements. This information can be entered manually, such as in a table or in fields of a data entry form.

Figure 3:
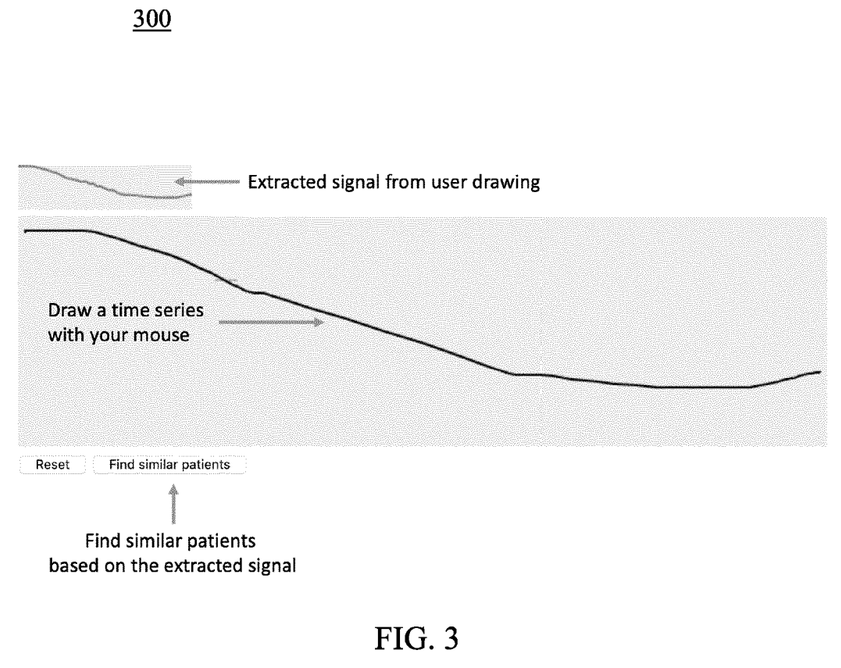
FIG. 3 is a schematic representation of a specialized user interface of a time series retrieval system, in accordance with an embodiment.

According to one embodiment, a query time series is provided via a specialized user interface system 300. Referring to FIG. 3, for example, is an embodiment of a specialized user interface system 300 utilized to receive a query time series. According to this embodiment, a user is presented with an interface that allows the user to draw or otherwise sketch a time series. The interface may be a local software-based interface, or may be a web-based interface, or may be any other interface configured to receive the query time series. The specialized user interface system 300 is configured to receive a drawn or sketch query time series, which is an improvement over existing user interfaces. The query time series may be provided to the interface using a stylus, finger, mouse, motion, or any other method of drawing or sketching a time series. In FIG. 3, for example, a user provides the query time series to the specialized user interface system using a mouse to simulate a graph of data over time. According to an embodiment, a query time series is then interpolated and extracted from the user drawing. Gaps in the user drawing or time series can be interpolated using forward filling.

According to an embodiment, the extracted query time series is then processed or otherwise analyzed by the trained encoder/decoder of the time series retrieval system. This results in the generation of a query time series context vector that represents the input provided by the user via the specialized user interface system of the time series retrieval system. The generated query time series context vector can be utilized immediately to query the database, or may be stored for future or downstream use.

At step 160 of the method, the time series retrieval system identifies one or more stored generated context vectors based on similarity to the query time series context vector. In other words, the generated query time series context vector is utilized to query the database of stored context vectors. Stored context vectors that are sufficiently similar to the query time series context vector can be identified, where sufficiently similar can be based on a threshold, user-defined parameters, a query algorithm, and/or a variety of other parameters. As an example, the context vectors may be indexed using a nearest neighbor algorithm, among other algorithms, such as a nearest neighbor algorithm that uses random projections to build a number of trees that can be efficiently searched. Accordingly, a distance metric such as a Euclidean or angular distant metric, can be utilized to identify the top K nearest neighbors to the query time series. Many other methods of identifying one or more stored generated context vectors based on similarity to the query time series context vector are possible.

At step 170 of the method, each of the identified one or more stored generated context vectors from step 160 of the method are utilized to retrieve the associated stored time series from the time series database using the using the trained time series encoder of the time series retrieval system. For example, each stored time series is associated in memory with the generated context vector, such that identification of the context vector enables retrieval from memory of the stored time series associated with an identified context vector. According to another embodiment, a generated context vector and the respective time series are associated with a unique ID or other identifier that connects a time series and its context vector to allow for identification and/or retrieval of one by identification of the other. Retrieval results in a retrieved time series for each of the identified one or more stored generated context vectors. These retrieved time series are more easily analyzed and reviewed by a user or other receiver of the results of a time series query. The retrieved time series may be immediately provided to the user, or may be stored for future or downstream use.

At step 180 of the method, the one or more retrieved time series are provided to a user via a user interface of the time series retrieval system. These retrieved time series may be provided to the user in any format. For example, the data may be provided as one or more graphs, tables, or other formats for analysis.

According to an embodiment, a retrieved time series is provided to a user via the user interface in such a way that the time series is associated with information about the source of the time series. Thus, the user can investigate or otherwise review the time series by interacting with the retrieved time series in the user interface, such as by selecting, reviewing, or otherwise manipulating the retrieved time series. For example, in the clinical setting, a time series can be associated with a patient, and clicking on the retrieved time series can reveal information about the patient such as a patient profile, demographics, treatment, health trajectory, and/or a wide variety of other information. Thus, according to an embodiment, a time series and/or context vector is associated or otherwise linked in memory to a source of information, such as contextual information, about that times series and/or context vector, such as the example of the patient profile.

Figure 4:
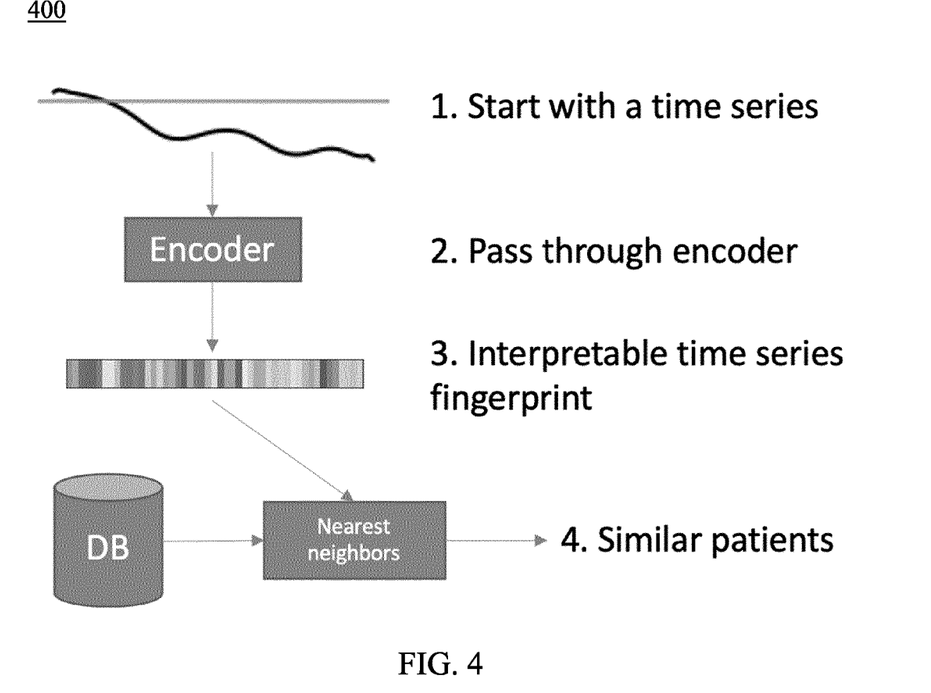
FIG. 4 is a flowchart of a method for identifying time series data using a time series retrieval system, in accordance with an embodiment.

Referring to FIG. 4 is another summary of a process 400 for querying a database of stored context vectors utilizing a query time series. At 1, a query time series is provided to the system via the specialized user interface system 300, such as by manual drawing of a representative query time series. At 2, the received query time series is analyzed by the encoder/decoder of the time series retrieval system. This results in the generation of a context vector, also called a fingerprint, at 3. At 4, the generated context vector is utilized to search a database of context vectors representing historical time series data to identify one or more similar time series, such as through a nearest neighbor approach.

Figure 5:
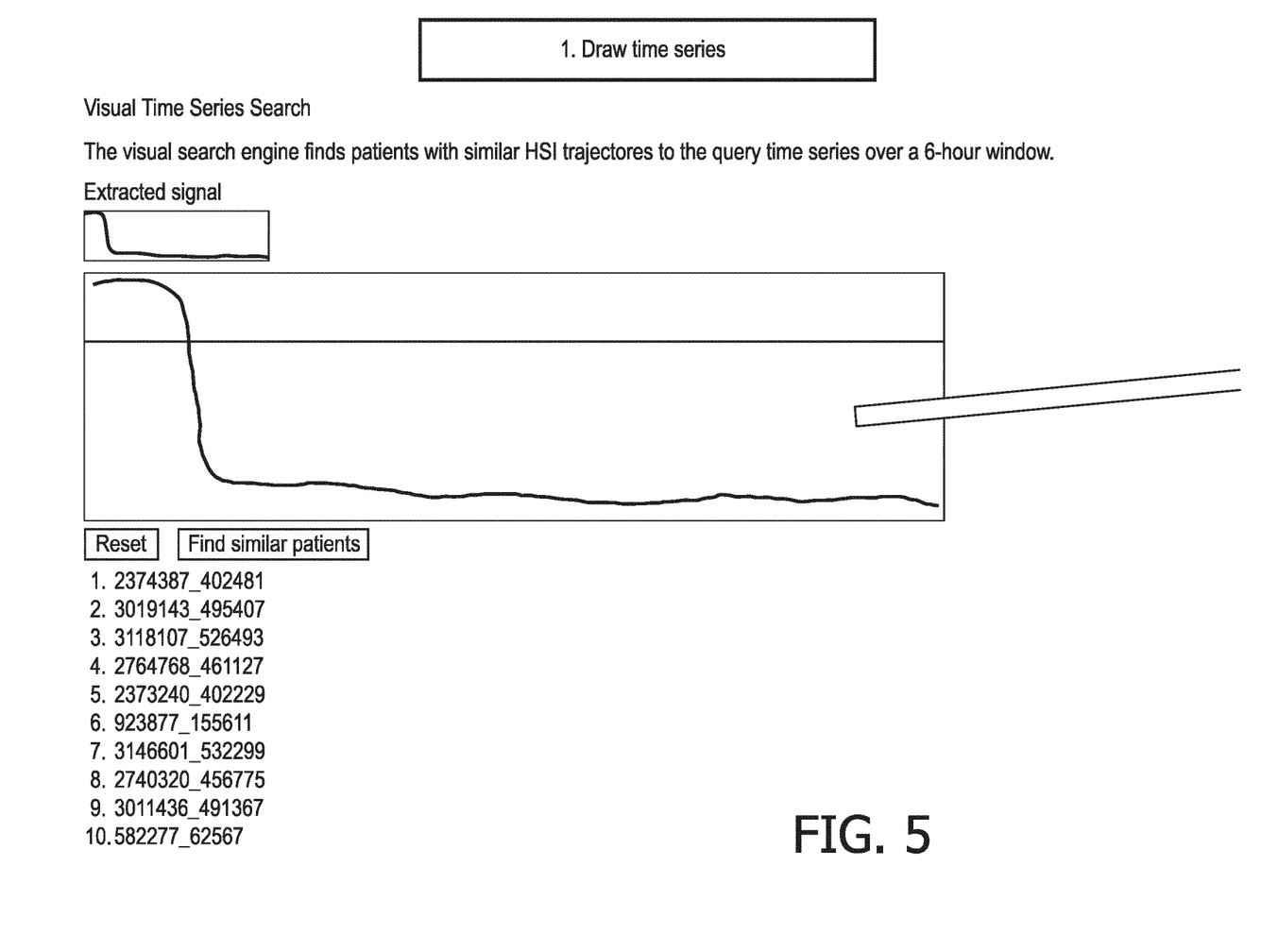
FIG. 5 is a schematic representation of a specialized user interface of a time series retrieval system, in accordance with an embodiment.

Referring to FIG. 5, in one embodiment, is an approach for identifying similar time series using a specialized user interface system. According to this embodiment, a user is presented with an interface that allows the user to draw or otherwise sketch a time series. The interface may be a local software-based interface, or may be a web-based interface, or may be any other interface configured to receive the query time series. At 1, the user draws a query time series using the specialized user interface. The system searches a database to identify one or more similar time series, and that data is provided to the user. In this embodiment, the query time series is utilized to identify a patient with a historical time series most similar to the query time series.

According to an embodiment, method 100 has many practical applications. For example, the method may be utilized to identify historical time series that follow a specific trajectory as a query time series, thus enabling quantification of outcomes of the historical time series and enabling prediction of future events of the query time series. As another example, the method may be utilized to identify cluster similar time series, and to quantify outcomes, treatments, and other aspects of the identified time series. In the clinical setting, for example, the method may be utilized to identify historical patients that follow a similar progression as a query time series representing a current patient, thereby enabling analysis or quantification of treatments, outcomes, and other aspects of the historical patients and how that might affect or impact the current patient. Many other practical applications are possible.

Figure 6:
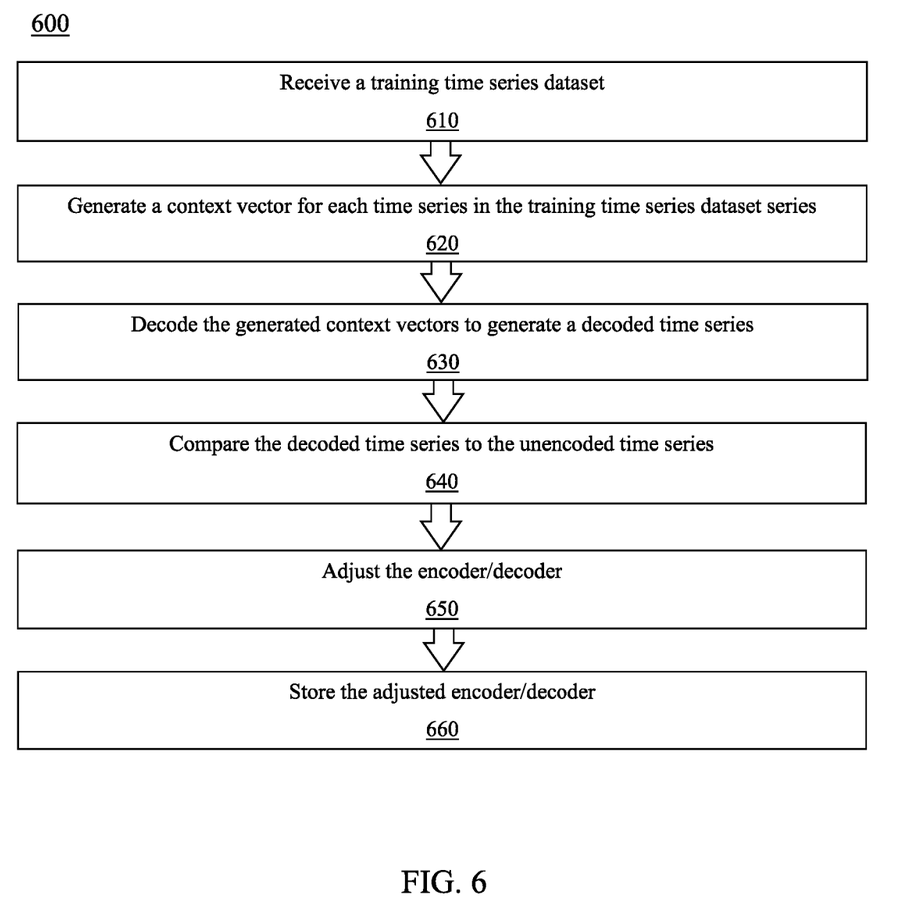
FIG. 6 is a flowchart of a method for training an encoder/decoder of a time series retrieval system, in accordance with an embodiment.

Referring to FIG. 6, in one embodiment, is a method 600 for generating or training a trained encoder/decoder of the time series retrieval system. According to an embodiment, the trained encoder/decoder may be any machine learning algorithm, neural network, or other methodology configured to convert a normalized and concatenated time series into a context vector or other numeric representation.

At step 610 of the method, the time series retrieval system receives a training time series dataset comprising a plurality of time series, each time series in the training time series dataset comprising a plurality of datapoints obtained over a time period. As expected, at least some of the plurality of times series in the training time series dataset comprise datapoints obtained at irregular time intervals within the time period. As just one example, the training time series dataset comprises monitoring and/or treatment data for a plurality of patients, although many other datasets are possible.

At step 620 of the method, a first version of the encoder/decoder of the time series retrieval system encodes each of the time series in the training time series dataset, thereby generating a context vector for each time series. The generated context vector can be stored or utilized immediately.

At step 630 of the method, the encoder/decoder of the time series retrieval system is utilized to decode the generated context vectors, thereby generating a decoded time series.

At step 640 of the method, the decoded time series is compared to the original unencoded time series in order to evaluate the accuracy of the encoder/decoder. In other words, the decoded time series is compared to the original unencoded time series to determine how well the encoder/decoder reconstructs the input data. As the encoder/decoder learns to reconstruct the input with greater accuracy, the mean squared error decreases and the encoder/decoder improves.

At step 650 of the method, if the decoded time series does not match or does not sufficiently match the original unencoded time series, the encoder/decoder can be adjusted or otherwise adapted or modified to improve reconstruction of input time series.

At step 660 of the method, the adjusted or modified encoder/decoder is selected or stored to be utilized for a next iteration of training, and/or for use by the system. For example, according to one embodiment, the encoder/decoder comprises one or more weights that can be adjusted and the weights can be stored for use in the next iteration of training of the encoder/decoder.

Figure 7:
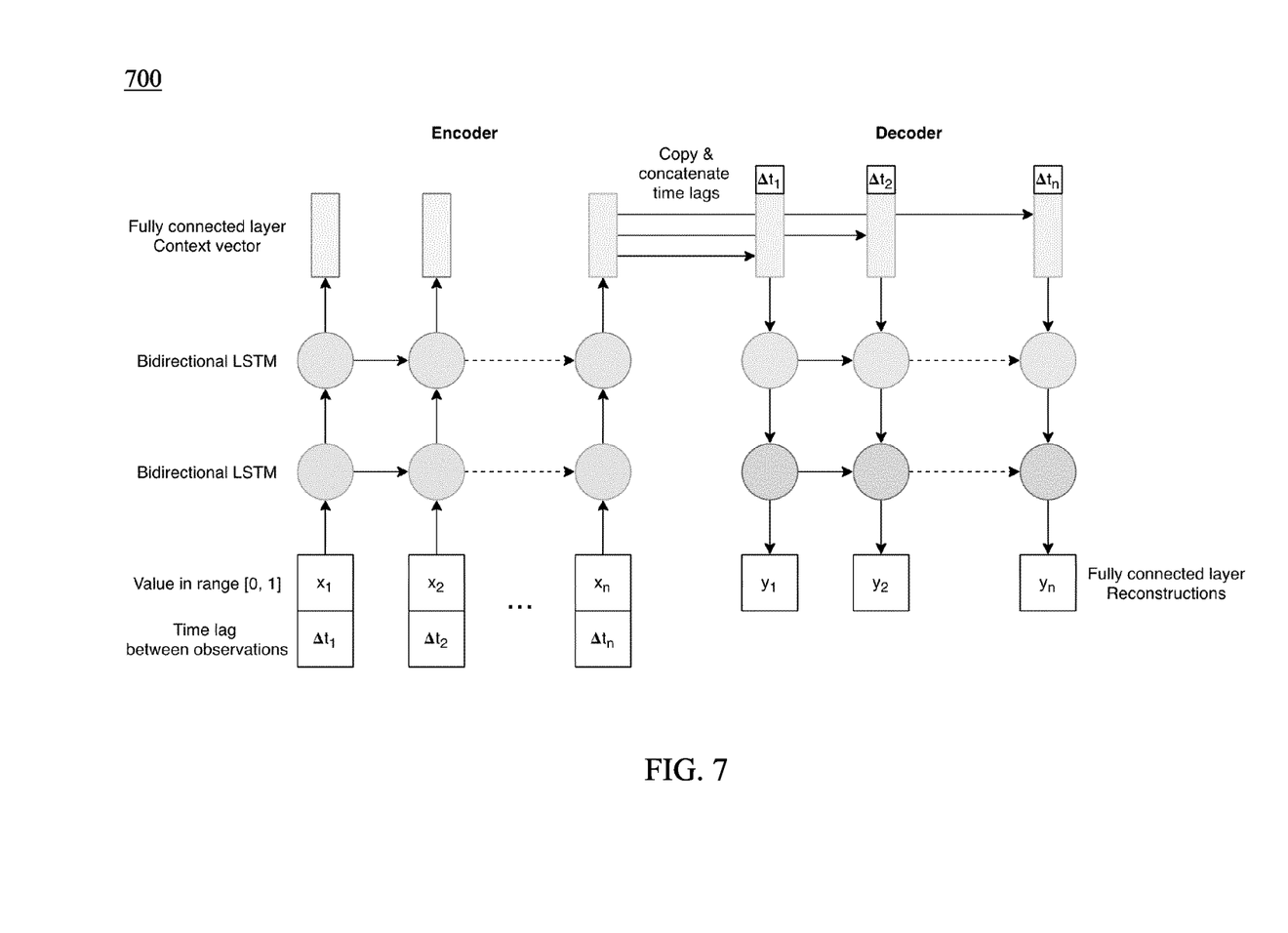
FIG. 7 is a schematic representation of an encoder/decoder of a time series retrieval system, in accordance with an embodiment.

Referring to FIG. 7, in one embodiment, is a schematic representation of an encoder/decoder of the time series retrieval system. According to an embodiment, the system comprises a plurality of time series. Each of the datapoints in the time series is normalized, such as to a value between 0 and 1, to generate normalized datapoints ($x_1, x_2, \ldots x_n$). Each normalized datapoint is concatenated with a time lag ($\Delta t$) between the datapoint and immediately preceding datapoint, thereby generating a time series comprising a series of normalized and concatenated points ($x_1/\Delta t_1, x_2/\Delta t_2, \ldots x_n/\Delta t_n$). The points are processed by one or more iterations or nodes of the encoder. For example, in FIG. 7 the encoder is a bidirectional long short-term memory (LSTM) recurrent neural network (RNN) architecture, although many other machine learning algorithms are possible. Processing by the encoder results in a generated context vector that represents the input time series. The context vector may be any length. According to an embodiment, the context vector comprises a length of eight, although many other lengths are possible. According to an embodiment, the output of the LSTM cell at the final time step and from the last layer is used as the context vector.

The encoder/decoder of the time series retrieval system is utilized to decode the context vectors, as shown in the right-hand side of FIG. 7. According to an embodiment, the generated context vector is copied and concatenated with the time lags and passed through the decoder, such as the network composes of LSTM cells as in FIG. 7. This generates a series of decoded data points ($y_1, y_2, \ldots y_n$) that represents the original time series. According to an embodiment, the decoded data points ($y_1, y_2, \ldots y_n$) can be compared to the input datapoints ($x_1, x_2, \ldots x_n$) to determine accuracy of the encoder/decoder.

Figure 8:
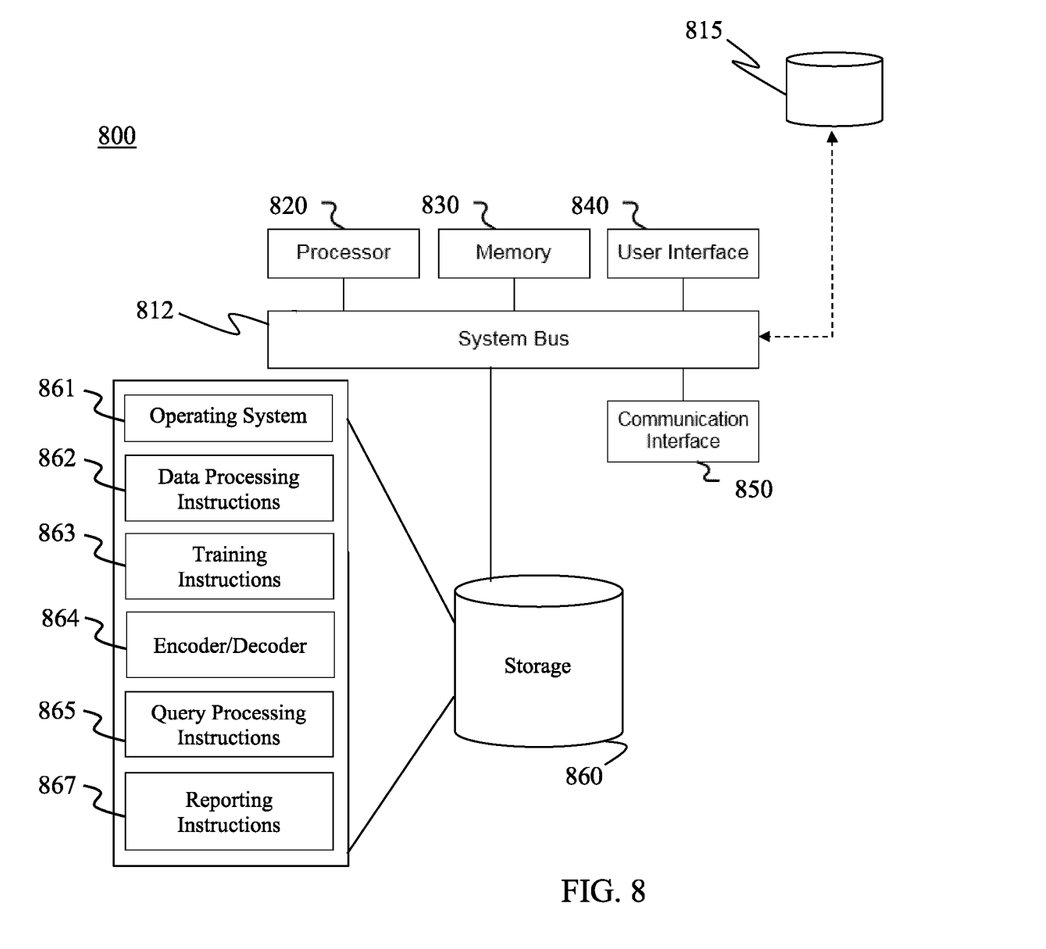
FIG. 8 is a schematic representation of a time series retrieval system, in accordance with an embodiment.

Referring to FIG. 8, in one embodiment, is a schematic representation of a time series retrieval system 800. System 800 may be any of the systems described or otherwise envisioned herein, and may comprise any of the components described or otherwise envisioned herein.

According to an embodiment, system 800 comprises one or more of a processor 820, memory 830, user interface 840, communications interface 850, and storage 860, interconnected via one or more system buses 812. It will be understood that FIG. 8 constitutes, in some respects, an abstraction and that the actual organization of the components of the system 800 may be different and more complex than illustrated.

According to an embodiment, system 800 comprises a processor 820 capable of executing instructions stored in memory 830 or storage 860 or otherwise processing data to, for example, perform one or more steps of the method. Processor 820 may be formed of one or multiple modules. Processor 820 may take any suitable form, including but not limited to a microprocessor, microcontroller, multiple microcontrollers, circuitry, field programmable gate array (FPGA), application-specific integrated circuit (ASIC), a single processor, or plural processors.

Memory 830 can take any suitable form, including a non-volatile memory and/or RAM. The memory 830 may include various memories such as, for example L1, L2, or L3 cache or system memory. As such, the memory 830 may include static random access memory (SRAM), dynamic RAM (DRAM), flash memory, read only memory (ROM), or other similar memory devices. The memory can store, among other things, an operating system. The RANI is used by the processor for the temporary storage of data. According to an embodiment, an operating system may contain code which, when executed by the processor, controls operation of one or more components of system 800. It will be apparent that, in embodiments where the processor implements one or more of the functions described herein in hardware, the software described as corresponding to such functionality in other embodiments may be omitted.

User interface 840 may include one or more devices for enabling communication with a user. The user interface can be any device or system that allows information to be conveyed and/or received, and may include a display, a mouse, and/or a keyboard for receiving user commands. In some embodiments, user interface 840 may include a command line interface or graphical user interface that may be presented to a remote terminal via communication interface 850. The user interface may be located with one or more other components of the system, or may located remote from the system and in communication via a wired and/or wireless communications network. According to an embodiment, the user interface 840 is the specialized and improved user interface described or otherwise envisioned herein.

Communication interface 850 may include one or more devices for enabling communication with other hardware devices. For example, communication interface 850 may include a network interface card (MC) configured to communicate according to the Ethernet protocol. Additionally, communication interface 850 may implement a TCP/IP stack for communication according to the TCP/IP protocols. Various alternative or additional hardware or configurations for communication interface 850 will be apparent.

Storage 860 may include one or more machine-readable storage media such as read-only memory (ROM), random-access memory (RANI), magnetic disk storage media, optical storage media, flash-memory devices, or similar storage media. In various embodiments, storage 860 may store instructions for execution by processor 820 or data upon which processor 820 may operate. For example, storage 860 may store an operating system 861 for controlling various operations of system 800.

It will be apparent that various information described as stored in storage 860 may be additionally or alternatively stored in memory 830. In this respect, memory 830 may also be considered to constitute a storage device and storage 860 may be considered a memory. Various other arrangements will be apparent. Further, memory 830 and storage 860 may both be considered to be non-transitory machine-readable media. As used herein, the term non-transitory will be understood to exclude transitory signals but to include all forms of storage, including both volatile and non-volatile memories.

While system 800 is shown as including one of each described component, the various components may be duplicated in various embodiments. For example, processor 820 may include multiple microprocessors that are configured to independently execute the methods described herein or are configured to perform steps or subroutines of the methods described herein such that the multiple processors cooperate to achieve the functionality described herein. Further, where one or more components of system 800 is implemented in a cloud computing system, the various hardware components may belong to separate physical systems. For example, processor 820 may include a first processor in a first server and a second processor in a second server. Many other variations and configurations are possible.

According to an embodiment, system 800 may comprise or be in remote or local communication with a database or data source 815. Database 815 may be a single database or data source or multiple. Database 815 may comprise the input data which may be used to train the encoder/decoder, as described and/or envisioned herein. For example, the database 815 may be a database of historical patient data, or any other historical data.

According to an embodiment, storage 860 of system 800 may store one or more algorithms and/or instructions to carry out one or more functions or steps of the methods described or otherwise envisioned herein. For example, the system may comprise one or more of data processing instructions 862, training instructions 863, an encoder/decoder 864, query processing instructions 865, and/or reporting instructions 867.

According to an embodiment, data processing instructions 862 direct the system to retrieve and process input data which is used to either: (i) train the encoder/decoder 864; or (ii) be processed by the encoder/decoder 864. The data processing instructions 862 direct the system to, for example, receive or retrieve time series training data to be used by the system as needed, such as from database 815 among many other possible sources. As described above, the input data can comprise a wide variety of input types from a wide variety of sources.

According to an embodiment, the data processing instructions 862 also direct the system to process the input data, such as by normalizing the data and concatenating the data with time intervals. This can be accomplished by a variety of embodiments for data processing. The outcome of the processing is normalized and concatenated data that can be utilized for training of the encoder/decoder, or can be utilized for similarity searching as described or otherwise envisioned herein.

According to an embodiment, training instructions 863 direct the system to utilize the processed data to train the encoder/decoder 864. The encoder/decoder can be, for example, any machine learning algorithm or method configured to encode and decode irregular time series data. According to an embodiment, the encoder/decoder comprises a bidirectional long short-term memory (LSTM) recurrent neural network (RNN) architecture, although many other architectures are possible.

According to an embodiment, query processing instructions 865 direct the system to enable receipt of, and processing of, a query time series. The system comprises a specialized user interface system that allows the user to draw or otherwise sketch a time series. The interface may be a local software-based interface, or may be a web-based interface, or may be any other interface configured to receive the query time series. The query time series may be provided to the interface using a stylus, finger, mouse, motion, or any other method of drawing or sketching a time series. According to an embodiment, a query time series is then interpolated and extracted from the user drawing by the query processing instructions 865.

According to an embodiment, reporting instructions 867 direct the system to generate and provide a report via the user interface comprising an identification of one or more time series similar to the query time series, as described or otherwise envisioned herein. According to an embodiment, a retrieved time series is provided to a user via the user interface in such a way that the time series is associated with information about the source of the time series. Thus, the user can investigate or otherwise review the time series by interacting with the retrieved time series in the user interface, such as by selecting, reviewing, or otherwise manipulating the retrieved time series. For example, in the clinical setting, a time series can be associated with a patient, and clicking on the retrieved time series can reveal information about the patient such as a patient profile, demographics, treatment, health trajectory, and/or a wide variety of other information. Thus, according to an embodiment, a time series and/or context vector is associated or otherwise linked in memory to a source of information, such as contextual information, about that times series and/or context vector, such as the example of the patient profile. Alternatively, the report or information may be communicated by wired and/or wireless communication to another device. For example, the system may communicate the report to a mobile phone, computer, laptop, wearable device, and/or any other device configured to allow display and/or other communication of the report.

According to an embodiment, the time series retrieval system is configured to process many thousands or millions of datapoints in the input data used to train the encoder/decoder, as well as in the comparison of a query context vector to the database of stored context vectors. For example, generated a functional and skilled trained encoder/decoder requires processing of millions of datapoints from input data. This can require millions or billions of calculations to generate a novel trained encoder/decoder from those millions of datapoints and millions or billions of calculations. As a result, each trained encoder/decoder is novel and distinct based on the input data and parameters of the machine learning algorithm. Thus, generating a functional and skilled trained encoder/decoder comprises a process with a volume of calculation and analysis that a human brain cannot accomplish in a lifetime, or multiple lifetimes.

By providing quick and easy identification of similar time series, this novel time series retrieval system has an enormous positive effect compared to prior art systems. As just one example in a clinical setting, by providing a system that can identify prognosis and/or treatment of historical patients relative to a current patient, the system can improve the survival outcomes and can lead to saved lives.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures.

What is claimed is:

1. A method for identifying time series data using a time series retrieval system, comprising:
    receiving, by the time series retrieval system, a plurality of time series, each time series comprising a plurality of datapoints obtained over a time period, wherein a least one of the plurality of times series comprises datapoints obtained at irregular time intervals within the time period;
    storing the received plurality of time series in a time series database of the time series retrieval system;
    for each of the received plurality of time series:
        normalizing each of the plurality of datapoints of the time series;
        concatenating, with each of the normalized plurality of datapoints, a time interval between the respective datapoint and an immediately preceding datapoint;
        generating from the normalized and concatenated time series, using a trained time series encoder/decoder of the time series retrieval system, a context vector for the time series; and
        storing the generated context vector in a context vector database of the time series retrieval system;
    receiving a request for identification of one or more of the plurality of time series based on similarity to a time series query, comprising: (i) receiving, via a user interface of the time series retrieval system, a query time series; and (ii) generating, using the trained time series encoder of the time series retrieval system, a query time series context vector;
    identifying, based on similarity to the query time series context vector, one or more of the stored generated context vectors;
    retrieving, from the time series database, each of the time series represented by the identified one or more stored generated context vectors; and
    providing, via the user interface of the time series retrieval system, the retrieved time series.

2. The method of claim 1, further comprising training the time series encoder/decoder of the time series retrieval system, comprising reiteration of:
    receiving a training time series dataset comprising a plurality of time series, each time series in the training time series dataset comprising a plurality of datapoints obtained over a time period, wherein at least some of the plurality of times series in the training time series dataset comprise datapoints obtained at irregular time intervals within the time period;

encoding, using the encoder/decoder of the time series retrieval system, a training time series of the training time series dataset to a context vector;

decoding, using the encoder/decoder of the time series retrieval system, the context vector to generate a decoded time series;

comparing the decoded time series to the original unencoded time series;

adjusting the encoder/decoder of the time series retrieval system, if the decoded time series does not sufficiently match the original unencoded time series; and storing the adjusted encoder/decoder of the time series retrieval system.

3. The method of claim 1, wherein the trained time series encoder comprises a neural network.

4. The method of claim 3, wherein the neural network is a bidirectional long short-term memory recurrent neural network.

5. The method of claim 1, wherein the one or more stored generated context vectors are identified based on a nearest neighbor method.

6. The method of claim 1, wherein each stored generated context vector is associated in memory with contextual information about the time series used to create the context vector.

7. The method of claim 1, wherein each of the plurality of time series comprises a plurality of datapoints obtained over a time period from a respective patient in a clinical setting.

8. The method of claim 1, wherein the query time series is generated by a user drawing a time series via the user interface of the time series retrieval system.

9. A time series retrieval system, comprising:

a plurality of time series, each time series comprising a plurality of datapoints obtained over a time period, wherein a least one of the plurality of times series comprises datapoints obtained at irregular time intervals within the time period;

a trained encoder/decoder configured to generate a context vector for each of the plurality of time series, resulting in a plurality of generated context vectors;

a database configured to store the plurality of time series and the plurality of generated context vectors;

a processor configured to: (i) receive a request for identification of one or more of the plurality of time series based on similarity to a time series query; (ii) identify, based on similarity to the query time series context vector, one or more of the plurality of generated context vectors, and wherein the trained encoder/decoder is further configured to retrieve from the database each time series represented by the identified one or more stored generated context vectors; and a user interface, wherein the user interface is configured to receive the time series query, and further configured to provide the retrieved time series.

10. The time series retrieval system of claim 9, wherein the trained time series encoder comprises a neural network.

11. The time series retrieval system of claim 10, wherein the neural network is a bidirectional long short-term memory recurrent neural network.

12. The time series retrieval system of claim 9, wherein the one or more stored generated context vectors are identified based on a nearest neighbor method.

13. The time series retrieval system of claim 9, wherein each stored generated context vector is associated in memory with contextual information about the time series used to create the context vector.

14. The time series retrieval system of claim 9, wherein each of the plurality of time series comprises a plurality of datapoints obtained over a time period from a respective patient in a clinical setting.

15. The time series retrieval system of claim 9, wherein the query time series is generated by a user drawing a time series via the user interface of the time series retrieval system.

* * * * *